United States Patent
Blatchley, III et al.

(10) Patent No.: US 7,842,512 B2
(45) Date of Patent: Nov. 30, 2010

(54) DYED MICROSPHERES FOR CHARACTERIZATION OF PHOTOCHEMICAL REACTOR BEHAVIOR

(75) Inventors: Ernest R. Blatchley, III, West Lafayette, IN (US); Chengyue Shen, West Lafayette, IN (US); Zorana Naunovic, West Lafayette, IN (US); Lian-Shin Lin, Morgantown, WV (US); Dennis A. Lyn, West Lafayette, IN (US); Donald E. Bergstrom, West Lafayette, IN (US); Shiyue Fang, Houghton, MI (US); Yousheng Guan, North Billerica, MA (US); Joseph Paul Robinson, West Lafayette, IN (US); Kathyrn E. Ragheb, West Lafayette, IN (US); Gerald J. Gregori, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 827 days.

(21) Appl. No.: 11/090,312

(22) Filed: Mar. 26, 2005

(65) Prior Publication Data

US 2006/0017008 A1    Jan. 26, 2006

Related U.S. Application Data

(60) Provisional application No. 60/557,020, filed on Mar. 26, 2004.

(51) Int. Cl.
*G01N 21/76*   (2006.01)
*G01N 33/533*  (2006.01)
*G01N 33/53*   (2006.01)
*F21V 9/16*    (2006.01)

(52) U.S. Cl. .................. 436/172; 436/546; 436/800; 436/805; 435/7.5; 435/968; 252/588

(58) Field of Classification Search ................. 436/544, 436/546, 164, 172, 800, 805; 435/7.5
See application file for complete search history.

(56) References Cited

U.S. PATENT DOCUMENTS 4,965,350 A * 10/1990 Inoue et al. ................. 536/22.1
6,027,855 A *  2/2000 Sokoluk et al. ........ 430/270.15

OTHER PUBLICATIONS

"Development of a Nucleoside Analog UV Light Sensor," by Shiyue Fang et al.; Nucleosides, Nucleotides & Nucleic Acids; vol. 22, Nos. 5-8; pp. 703-705; 2003.

(Continued)

*Primary Examiner*—Shafiqul Haq
(74) *Attorney, Agent, or Firm*—Brinks Hofer Gilson & Lione

(57) ABSTRACT

A method for photochemical reactor characterization includes an application of using dyed microspheres exposed to UV irradiation under a collimated-beam system. Particle specific fluorescence intensity measurements are conducted using samples form the collimated beam and flow-through reactor results using flow cytometry. A numerical model may be used to simulate the behavior of the reactor system to provide a particle-tracking algorithm to interrogate the flow and intensity field simulations for purposes of developing a particle specific estimate of the dose delivery. A method for measuring UV dose distribution delivery in photochemical reactors is provided that includes introducing microspheres labeled with a photochemically-active compound in a UV reactor. The labeled microspheres are harvested downstream of the irradiated zone of a UV reactor and exposed to UV irradiation under a collimated beam of UV irradiation. The method further includes quantifying a UV dose-response behavior, conducting fluorescence intensity measurement on the labeled microspheres from the UV reactor, and developing an estimate of a dose distribution delivered by a UV reactor based on the numerical deconvolution of the sum of the UV dose response behavior and fluorescent intensity of exposed microspheres.

16 Claims, 8 Drawing Sheets

OTHER PUBLICATIONS

"Dyed Microspheres for Quantification of UV Dose Distributions: Photochemical Reactor Characterization by Lagrangian Actinometry," by Ernest R. Blatchely III et al.; 27 pages.

Shiyue Fang, Yousheng Guan, Ernest R. Bletchley III, Lian-Shin Lin, Cheng Yue Shen, and Donald E. Bergstrom, entitled "Development of a Nucleoside Analog UV Light Sensor," Nucleosides, Nucleotides & Nucleic Acids, vol. 22, Nos. 5-8, pp. 703-705, 2003.

Shiyue Fang, Yousheng Guan, Ernest R. Bletchley III, Lian-Shin Lin, Cheng Yue Shen, and Donald E. Bergstrom, entitled "Development of a Nucleoside Analog UV Light Sensor," Published in Nucleosides, Nucleotides & Nucleic Acids, vol. 22, Issue 5-8; Oct. 8, 2003; pp. 703-705; on-line Article.

W.A. Anderson, L. Zhang, S.A. Andrews, J.R. Bolton, entitled "A Technique for Direct Measurement of UV Fluence Distribution," AWWA Water Quality Technology Conference, Proceedings, Nov. 2-6, 2003.

Zuzana Bohrerova, Gil Bohrer, S. Mohan Mohanraj, Joel Ducoste, and Karl G. Linden, entitled "Experimental Measurements of Fluence Distribution in a UV Reactor Using Fluorescent Microspheres," Environmental Science & Technology, vol. 39, No. 22, Oct. 7, 2005, pp. 8925-8930.

Ernest R. Blatchley, III, et al., "*Dyed Microspheres for Quantification of UV Dose Distributions: Photochemical Reactor Characterization by Lagrangian Actinometry*," Journal of Environmental Engineering, Nov. 2006, 1390-1403, vol. 132, No. 11.

* cited by examiner

Dashed line = excitation
Solid line = emission

| $\lambda$ (nm) | $\Phi_\lambda$ (mole/Einstein) (mean ± std. dev.) |
|---|---|
| 222 | 0.693 ± 0.037 |
| 254 | 0.732 ± 0.064 |
| 282 | 0.850 ± 0.049 |

DYED MICROSPHERES FOR CHARACTERIZATION OF PHOTOCHEMICAL REACTOR BEHAVIOR

RELATED APPLICATIONS

The present document claims the benefit of the filing date under 35 U.S.C. §119(e) of Provisional U.S. Patent Application Ser. No. 60/557,020, filed Mar. 26, 2004, which is hereby incorporated by reference.

BACKGROUND

1. Technical Field

This invention relates generally to methods for photochemical reactor characterization. More particularly, this application is related to a method of using dyed microspheres exposed to UV radiation to measure the dose distribution delivered by the reactor for any given set of operating conditions.

2. Background Information

Ultraviolet (UV) systems have been used for the treatment of aqueous liquids, particularly in disinfection applications. In the past, several thousand UV based disinfection systems have been installed and placed into operation throughout the United States and Europe. These systems are an alternative to conventional chlorine-based disinfection and their emergence may be attributed to their comparative small size, low cost, simplicity, antimicrobial efficacy, and "environmental friendliness" relative to existing chlorine-based systems.

Traditionally, the application of UV irradiation for disinfection has been directed to conventional wastewater disinfection. More recently, this application has expanded to include wastewater reuse and potable water supplies. Discoveries of the effectiveness of UV irradiation for inactivation of protozoan (oo)cysts suggest that UV irradiation could be used with increasing regularity as a disinfection alternative.

UV irradiation has also been shown to be effective for the inactivation of the spores of *Bacillus anthracis*, thereby suggesting that UV irradiation could also be used for maintaining the security of public water supplies against intentional or unintentional contamination by biological warfare agents.

UV reactors used in treatment operations deliver a distribution of UV doses to particles that pass through them, where the UV dose is defined as the time-integral of UV intensity history over the period of exposure. The variation in the dose delivery within such a system, even when operated under steady state conditions, is attributable to the heterogeneity in the radiation intensity field and turbulence within the flow field. The efficiency of photochemical reactors, including those used for disinfection of water, has been shown to be governed by the distribution of UV doses delivered to particles that traverse the irradiated zone of these systems.

Efforts to characterize the performance of UV systems have involved using estimates of the average UV dose delivered by the reactor. Although several methods exist for estimation of "average UV dose", all suffer from the fact that they represent gross oversimplifications of reactor performance.

One of the problems with using an "average UV dose" is that any reactor modifications relating to improvements in the performance of the process or the reactor efficiency are minimized or in sometimes not included in the analysis of the performance of the UV system. For example, one approach has demonstrated that the inclusion of internal mixing components, in otherwise conventional UV system configurations, can yield increases in antimicrobial efficacy of 100% or more. These modifications, however, result in minimal, if any, change in the "average UV dose" delivered by the UV system.

Currently, the only methods available to estimate the UV dose distribution involve using numerical simulations of process behavior, usually involving a component approach. The intensity field may be simulated using one of several available models. Computational fluid dynamics (CFD) are commonly used to represent the flow field, including its turbulence characteristics. The results of these simulations are integrated to provide a representation of the dose distribution. Most such simulations employ a Lagrangian (particle centered) approach, in which a particle-tracking algorithm is used to interrogate the simulated flow field and simulate individual particle trajectories. In a Lagrangian modeling approach, dose increments are assigned to each particle step within its simulated trajectory, such that an estimate of particle-specific dose may be assigned to each simulated particle trajectory. By repeating this process for a large population of particles, it is possible to close on a stable dose distribution estimate.

Among the methods used to estimate average UV dose, the two most common involve a simple numerical simulation and a set of experimental measurements, respectively. The first method involves numerical approximation of the product of the spatial average of radiation intensity within the reactor ($I_{avg}$) and the mean hydraulic detention time ($\theta$). This method of the reactor characterization is simple to complete but yields unreliable, often misleading predictions of reactor performance.

The second method of reactor characterization is known as biodosimetry. In biodosimetry, a challenge organism is imposed on an actual continuous flow reactor. Reactor performance is quantified by measuring the concentration of the viable challenge organisms in the influent and effluent streams. The UV dose-response behavior of the challenge organism is measured over a range of UV doses using a collimated beam with a shallow, well-mixed batch reactor to accomplish irradiation. The effective dose, which is sometimes referred to as the "reduction equivalent dose," is defined as the dose delivered by the collimated beam that accomplishes the same extent of inactivation as the follow through reactor.

Biodosimetry is the most commonly applied method for reactor characterization and has been defined as an acceptable method of reactor validation for potable water UV disinfection systems in the United States and much of Western Europe. It is also well known, however, that the results of biodosimetry are not useful for quantitative prediction of the inactivation of waterborne microorganisms, other than those used as challenge organisms. Therefore, it is difficult to obtain an accurate, quantitative prediction of microbial inactivation from biodosimetry results for any organism that has UV dose-response behavior different from the challenge microorganism(s).

Furthermore, biodosimetry provides no information about the dose distribution. Without this information, it is not possible to develop an accurate prediction of microbial inactivation for the wide spectrum of waterborne microorganisms that could be imposed on a UV system. In spite of this shortcoming, biodosimetry exists as the standard method for characterization of UV reactors. Biodosimetry has been the most widely used tool for UV system characterization, particularly given the skepticism that accompanies reactor characterization by purely numerical methods, such as the Lagrangian model discussed above. Limitations of biodosimetry have been recognized for many years. The development of standardized techniques for dose characterization has been identified as a top research priority among researchers involved in UV disinfection.

Another important shortcoming of conventional photochemical reactor design and analysis has been the lack of a mechanism or protocol for estimating the distribution of UV doses delivered by the system. In reality, the three-dimensional nature of the velocity and intensity fields of these systems dictates that all continuous-flow UV systems will deliver a broad distribution of doses.

With the recent discovery of the effectiveness of UV irradiation for disinfection of drinking water, there is need for the development of methods of reactor validation and testing. Currently, there is tremendous interest in the application of UV irradiation as a disinfection process for the production of drinking water, although relatively few utilities currently employ UV-based processes. Reactor validation and testing are accomplished using relatively crude, empirical methods, such as biodosimetry. These methods provide index measurements of reactor behavior, but cannot be used to make quantitative predictions of reactor performance or efficiency.

There is also need for practical tools to assess the efficiency and reliability of a UV system available to UV system designers, regulators and treatment facility operators. These tools should be universal and enable comparisons of different UV systems as well provide for accurate and reliable predictions of inactivation of all waterborne microorganisms.

Although, several experiment-based methods are available for characterization of UV reactors, as discussed in the preceeding paragraphs, these methods do not yield an estimate of the dose distribution delivered by the system. In most instances, the reactor performance is characterized using a grossly over simplified representation of reactor behavior. Consequently, existing experimental methods do not yield information that may be used for quantitative assessment of photochemical reactor performance. Thus, there is a need for a method to measure the UV dose distribution delivery in photochemical reactors that can provide accurate assessment of photochemical reactor performance.

BRIEF SUMMARY

A method is presented for measurement of UV dose distributions delivered in photochemical reactor systems. A dye molecule is attached to a microsphere. The dye molecule may be attached to the microsphere by any known means. The dye is selected such that its fluorescence characteristics change as a result of UV exposure. As such, the dose of radiation delivered to each dyed microsphere may be quantified by measuring the fluorescence intensity of the microsphere. Dyed microspheres are introduced to the influent of a photochemical reactor system. The microspheres are collected downstream of the UV reactor.

An extracted sample of the suspended dyed microspheres is subjected to a range of single-valued, quantifiable doses using a shallow, well-mixed batch reactor under a collimated beam of UV radiation, or another device that can meet these objectives. Samples collected after UV exposure, collected either in the effluent of the continuous-flow reactor or from the collimated-beam system, are subjected to physical separation processes to allow concentration of the microspheres prior to analysis by flow cytometry. Flow cytometry is used to provide measurements of fluorescence intensity for individual particles within a population of particles collected post-UV exposure. Data from these analyses is subjected to a numerical deconvolution algorithm to allow estimation of the dose distribution delivered by a photochemical reactor A method for measuring UV dose distribution delivery in photochemical reactors is also provided including the steps of: introducing microspheres labeled with a photochemically-active compound in a UV reactor; harvesting the labeled microspheres downstream of the irradiated zone of a UV reactor; exposing the labeled microspheres to UV irradiation under a collimated beam of UV irradiation and quantifying a UV dose-response behavior; conducting fluorescence intensity measurement on the labeled microspheres from the UV reactor; and developing an estimate of a dose distribution delivered by a UV reactor based on the numerical deconvolution of the sum of the UV dose response behavior and fluorescent intensity of exposed microspheres.

In an alternate method of using dyed microspheres to calculate a UV dose, comprising the steps of: introducing a non-fluorescent compound into an inlet of a photochemical reactor wherein the non-fluorescent compound attaches to a microsphere to form a dyed microsphere; measuring distribution of the UV dose; using a mathematical algorithm to simulate the estimate of the UV dose; and recording the intensity and numerical value of the UV dose over a period of exposure on a graph.

A method for measuring UV dose distribution delivery in photochemical reactors is also provided, comprising the steps of: introducing a non-fluorescent compound in the inlet of a photochemical reactor system wherein the non-fluorescent compound attaches to a microsphere; collecting the attached non-fluorescent compound microsphere forms a dyed microsphere that passes through the photochemical reactor system; measuring the fluorescence intensity of attached non-fluorescent compound microsphere in response to UV radiation; and quantifying the dose distribution delivery of the system.

BRIEF DESCRIPTION OF THE DRAWINGS

FIG. 3 is summary of the quantum yield estimates for photoconversion of the dye to a fluorescent product;

DETAILED DESCRIPTION OF THE DRAWINGS AND THE PRESENTLY PREFERRED EMBODIMENTS

To help understand this description, the following definitions are provided with reference to terms used in this application. Throughout this specification and in the appended claims, when discussing the application of this invention to photochemical characterizations, the term "photochemical reactor" with respect to such an application is intended to refer to a closed or open vessel containing UV sources, and through which a fluid is passed to accomplish treatment.

The term "UV radiation" means electromagnetic radiation characterized by wavelengths of 10-400 nm. For water treatment applications, the relevant wavelength range is approximately 200-300 nm, corresponding to radiation that is effective in penetrating water and that demonstrates germicidal or photochemical activity.

The term "microspheres" describes spherical objects with size on the order of a few μm, usually constructed of a polymeric material.

The term "UV dose" means the time-integral of radiation intensity over the period of exposure.

The term "challenge organism" is intended to refer a microorganism used in a biodosimetry assay.

The term "flow cytometry" refers to an analytical method for measuring optical characteristics of individual particles.

The term "treated water" refers to water that has been subjected to treatment for improving its quality.

Figure 8:
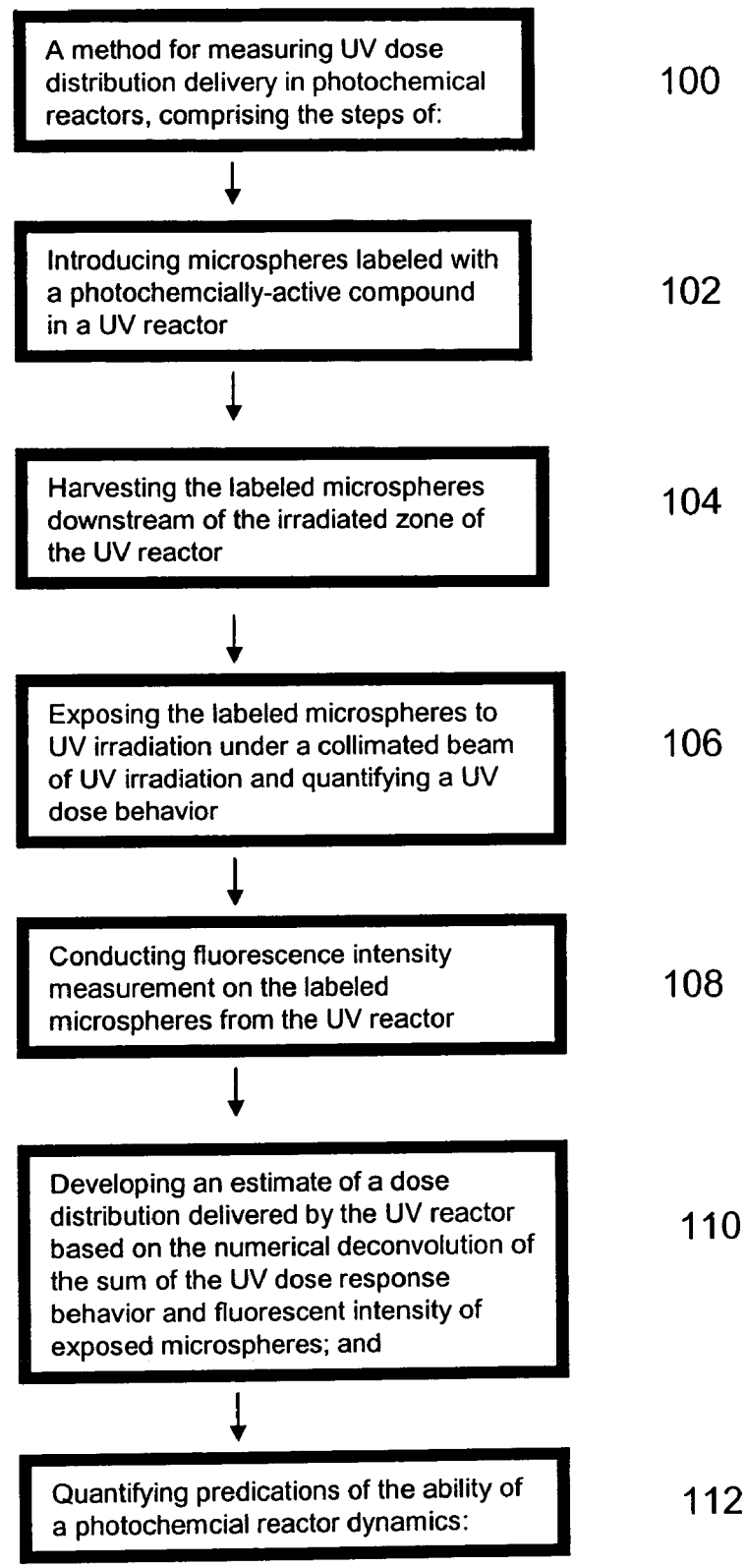
FIG. 8 shows a flow chart illustrating the steps comprising a method of the present invention.

This invention is relates to a method using dyed microspheres for measurement of the ultraviolet (UV) dose distribution delivered by a continuous-flow UV reactor. Ultraviolet dose distribution delivery in these reactors may be measured by introducing microspheres labeled with a photochemically-active compound in a UV reactor; harvesting the dyed microspheres downstream of the irradiated zone of the UV reactor; exposing the labeled microspheres to UV irradiation under a collimated beam of UV irradiation and quantifying a UV dose behavior; conducting fluorescence intensity measurement on the labeled microspheres from the UV reactor; developing an estimate of a dose distribution by the reactor by numerical deconvolution of the sum of the UV dose response behavior and fluorescent intensity of exposed microspheres; and quantifying predication of the ability of the photochemical reactor dynamics. For purposes of understanding this method, the figures are discussed in specific detail. Preferably the steps of this method are shown in FIG. 8. However, not all of the steps disclosed must be included and the arrangement of the steps may vary as needed to practice the method.

Figure 1:
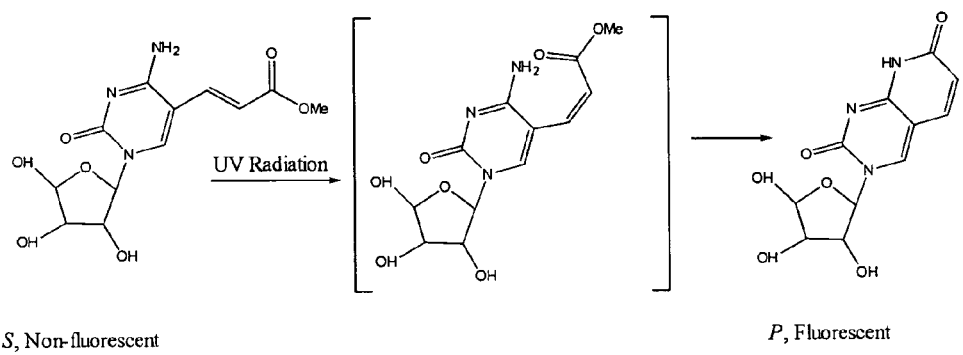
FIG. 1 is a schematic illustration of the ultraviolet photochemistry of a non-fluorescent dye in aqueous solution.

FIG. 1. illustrates a basic ultraviolet (UV) photochemistry of a non-fluorescent compound or dye in an aqueous solution. As shown in FIG. 1, a non fluorescent compound is introduced in to the UV reactor system. Preferably, the non-fluorescent molecule is (E)-5-[2-(methoxycarbonyl)ethenyl]cytidine (MW 327.3, hereafter referred to as S) such that when S is subjected to UV irradiation, S is transformed to a stable brightly violet fluorescent product, 3-β-D-ribofuranosyl-2,7-dioxopyrido[2,3-d]pyrimidine (MW 295.26, hereafter referred to as P). S can exist in various compositions such as a solid state or aqueous composition. During UV irradiation, S transforms to a chemical compound having an increased fluorescent composition. Preferably, the fluorescence levels of the stable compound may be measured.

Figure 2:
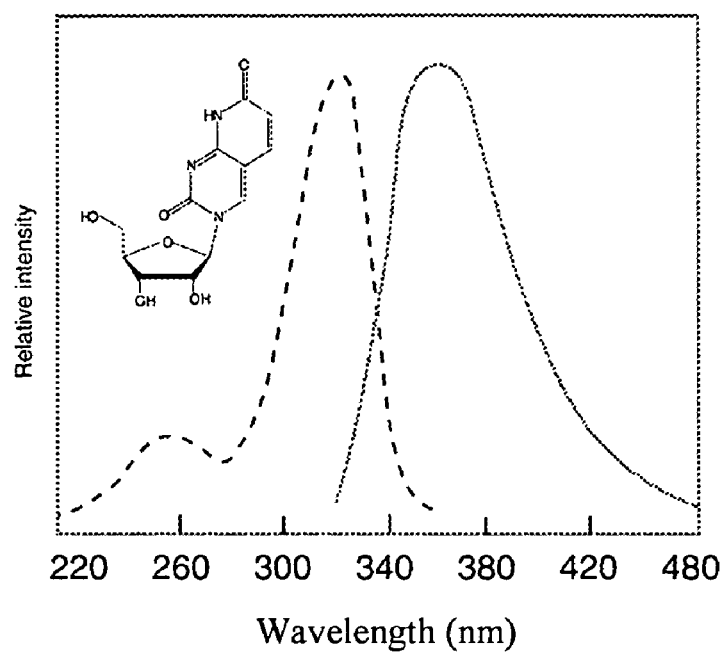
FIG. 2 is a graphical representation of the fluorescence excitation and emission characteristics of the photoproduct of a dye in an aqueous solution.

As shown in FIG. 2, the stable photoproduct, P, has a fluorescence excitation maximum at 330 nm and an emission maximum at 385 nm. As such, S, may be differentiated from P on the basis of a fluorescence measurement. Alternate chemical compounds may be used as a dye for attaching to the microsphere but the chemical compound should not interfere with the photochemistry of S or the fluorescence behavior of P.

In FIG. 3, the chart provides estimates of the quantum yield for photoproduction of the non-fluorescent compound to a fluorescent compound. The quantum yield for phototransformation of S to P in homogeneous aqueous solution may be measured at three germicidally-active UV wavelengths as desired. In the absence of UV radiation, S and P are stable. Dyed microspheres are sensitive to UV irradiation. In this method, S is attached to the microspheres in a manner such that the basic photochemistry of S is not adversely affected, and the fluorescence signal of the photoproduct P is not eliminated. This attachment may be achieved using a streptavidin-biotin linkage using a long hydrophilic linker.

Non-fluorescent molecule S can be attached to a microsphere in any manner that does not adversely affect the $UV_{254}$ photochemistry of S, or the fluorescence behavior of the (fluorescent) photoproduct (P). The amino and the α,β-unsaturated methyl ester functionalities in S, as well as the heterocyclic ring, are preferably left unmodified during the attachment to the microsphere. Two strategies can be used to attach S to a microsphere in a manner that prevents quenching of P. First, polystyrene beads coated with the protein streptavidin, which has a minimal absorption above 300 nm (excitation maximum for P are 330 nm and 385 nm), can be selected as the microspheres (i.e., the starting material). One advantage of using these microspheres arises from the hydrophilic nature of their surfaces, which can stabilize their suspension in water and prevent their self-aggregation. Second, a long hydrophilic linker between S and the microsphere can be employed to minimize any possible energy transfer between them. Attachment of S to microspheres can be accomplished using a biotin-streptavidin linkage. The long hydrophilic linker can also favor the non-covalent bonding between biotin and streptavidin. The synthesis of the biotinylated dye molecule 7 was performed as described Scheme 1:

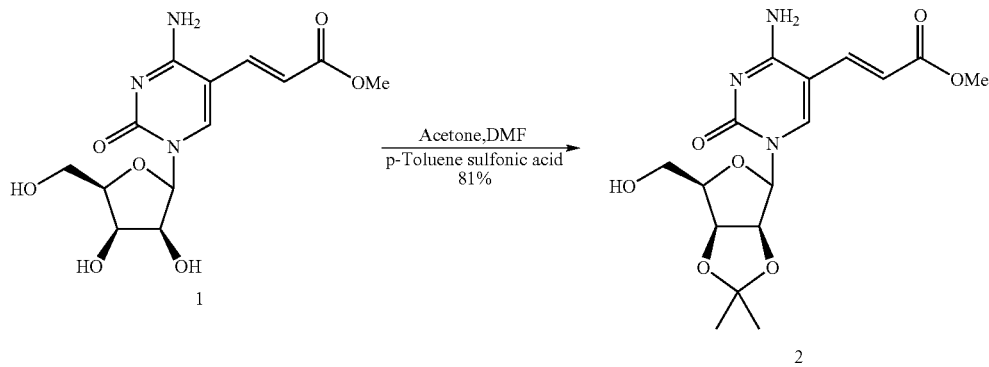

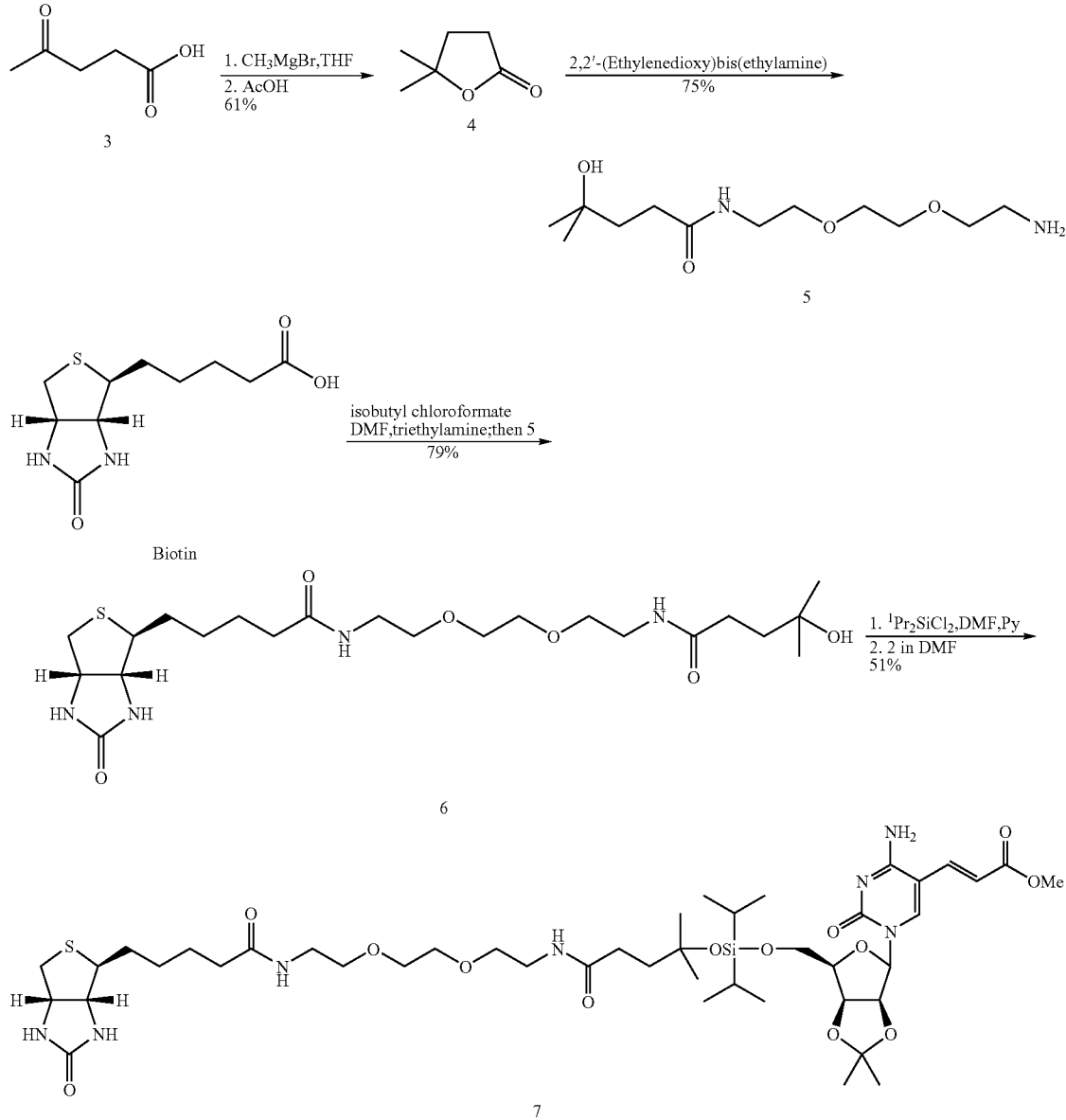

With reference to Scheme 1 above, a cytidine derivative 1 was transformed to a less hydrophilic molecule 2 by protecting the 2',3'-hydroxyl groups in a mixture of anhydrous acetone and DMF in the presence of p-toluenesulfonic acid (81%). A hydrophilic linker, such as an aminoalcohol 5, was prepared from commercially available levulinic acid in two steps. Treatment of the levulinic acid (3) with 2 equivalents of $CH_3MgBr$ in THF followed by AcOH gave the lactone 4 (61%). The Lactone 4 was heated with 2,2'-(ethylenedioxy) bis(ethylamine) in water, to give 5 as a light yellow oil in 75% yield. Biotinylation of 2 was accomplished in two steps. The carboxylic acid group in biotin was activated with isobutyl chloroformate in DMF, without isolation and purification. The intermediate was reacted with 5 in situ to give the biotinylalcohol 6 (79%). The hydroxyl group in 6 was silylated with diisopropyldichlorosilane in DMF in the presence of pyridine giving a clear light yellow solution. This solution was added to a solution of 2 in DMF, and the target biotinylated dye molecule 7 was obtained in 51% yield. Next, 7 was attached to streptavidin-coated microspheres (Polysciences, Inc. Warrington, Pa., 6.0 mm, 42.29 mg/ml biotin binding capacity, 1.05 g/mL specific gravity) by simple incubation in TTL buffer (100 mM Tris-HCl, pH 8.0, 0.1% Tween 20, 1 M LiCl) at room temperature for 12 hours. Excess 7 was removed by washing with water to produce the dye-loaded microspheres. The dye-loaded microspheres can be stored in water at 4° C. in the dark for up to two weeks without substantial change in their fluorescence characteristics.

The extent of dye conversion for an individual microsphere will depend of the dose of UV radiation to which the microsphere has been exposed. Each dyed microsphere will follow a different trajectory through a continuous-flow system; therefore, each microsphere will receive a different dose. Collection and analysis of a large population of microspheres from the effluent of a continuous-flow reactor allows measurement of the UV dose distribution delivered by the reactor.

The results from the photochemical process can vary depending upon the dose of radiation delivered to the photochemical target (i.e. the parent compound). Preferably, for a UV-based photochemical reactor systems used in treatment of fluids, the reactor behavior may be influenced by the existence of various characteristics in the system. Inherently, these characteristics control the dose distribution delivery by the system.

A validated numerical simulation may be used for characterization of the UV reactor properties. Each component of the simulation model may be validated independently using separate physical measurements. The UV dose-response behavior of the dyed microspheres may be measured using a process where sub-samples of an aqueous suspension of the dyed microspheres are subjected to UV irradiation under a collimated-beam device, in a shallow, well-mixed batch reactor. Subsequently, the particle-specific fluorescence intensity (FI) of the UV-irradiated microspheres may be measured using flow cytometry. The measurement extracted samples then may be analyzed with a data rate of approximately 150-200 particles per second. The extracted samples may be measured using different data rates as desired.

The dyed microspheres are excited using the output of a laser output characteristics that match the excitation behavior of the fluorescent photoproduct. Subsequently, the linear fluorescence signal may be measured, at a wavelength that corresponds to the emission behavior of the fluorescent product. The forward angle light scatter, which is size related, and orthogonal light scatter, which is shape and structure related, are collected and documented. The dyed microspheres may be concentrated prior to flow cytometry analysis. For example, the dyed microspheres may be concentrated using membrane filtration, resuspension in an aqueous buffer, and centrifugation.

Figure 4:
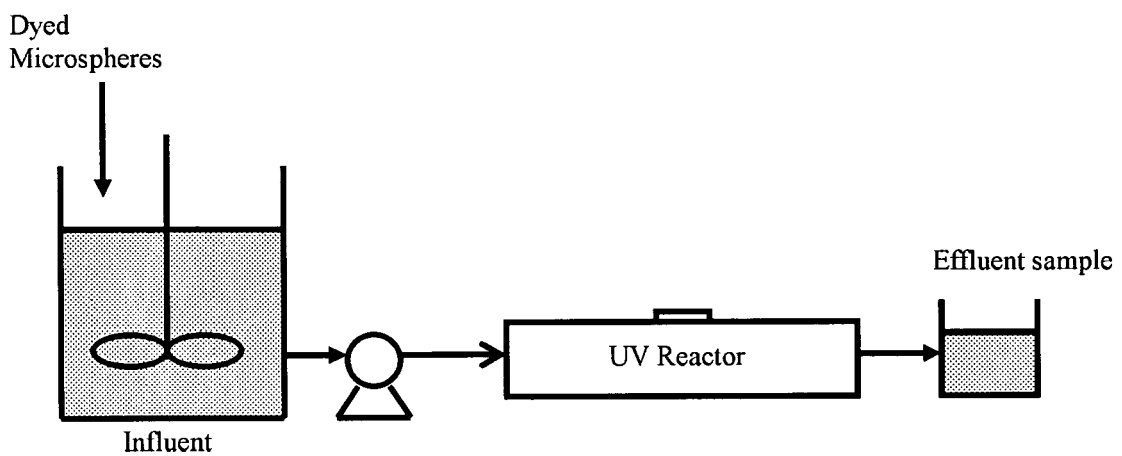
FIG. 4 is a schematic illustration of the introduction of dyed microspheres to a continuous-flow reactor.

FIG. 4 a schematically illustrates the step for producing a detailed description of the UV dose-response of the dyed microspheres. Treated water collections from the UV reactor are prepared by physically separating the water from the microspheres. The dyed microspheres may be concentrated using membrane filtration, resuspension in an aqueous buffer, and centrifugation. The aqueous suspension of the dyed microspheres may be pumped through a single-lamp, continuous-flow UV reactor system.

In conjunction with the procedure described above, the collimated-beam system may be used to develop a detailed description of the UV dose-response behavior of the dyed microspheres. The aqueous microsphere suspensions may be exposed in doses ranging from 0-200 mJ/cm$^2$. The range of doses may vary as desired. The range, however, is preferably representative of the range of doses that can be delivered by the continuous-flow reactor for the relevant range of operating conditions.

Figure 5:
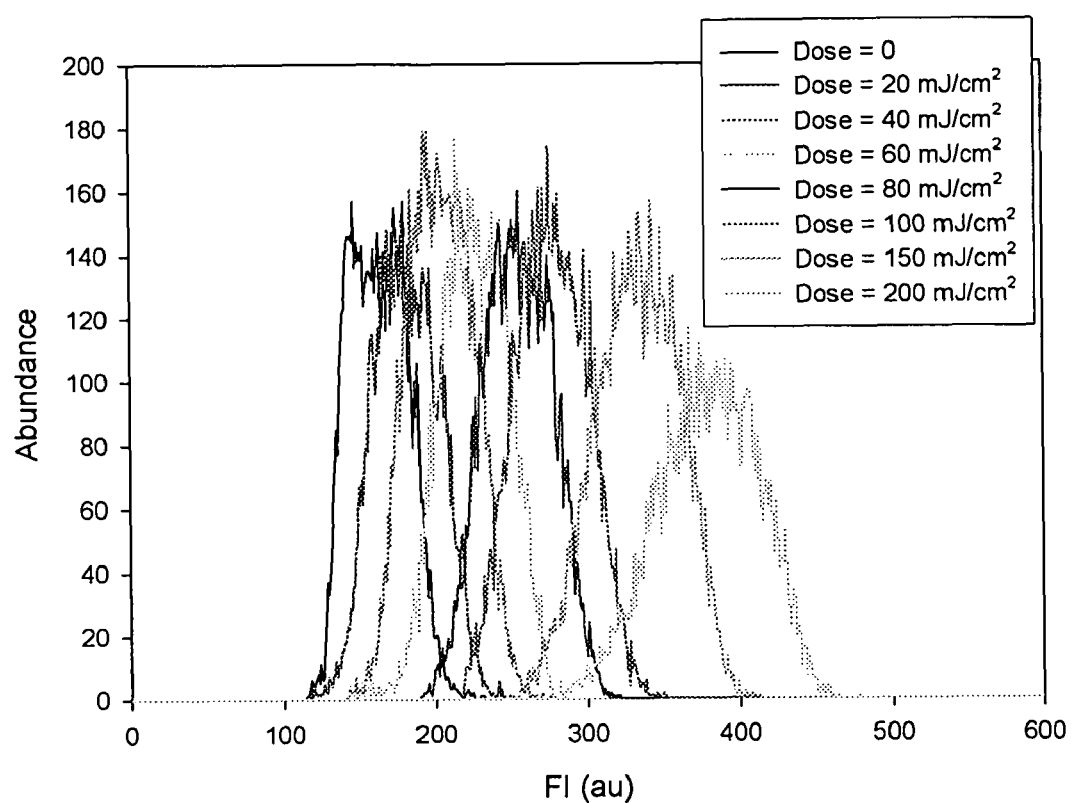
FIG. 5 is a graphical representation of fluorescence intensity distributions of dyed microspheres generated using a collimated beam system.

FIG. 5 provides a graphical representation of the results of flow cytometry analyses of the dose-response behavior of the dyed microspheres. The FI distributions, as illustrated in FIG. 5, correspond to the various extracted samples of the dyed microspheres from the dose-response collimated-beam step. Preferably, as the FI increases monotonically with each UV dose as a result of the photoproduction of P from S. Although each of the collections from the collimated-beam step is subjected to a single-valued dose, the distribution of FI exists among all of the exposed microspheres. Variations in the FI measurements may be attributed to the intrinsic non-homogeneity of the dyed microspheres. For example, each dyed microsphere may have a different size, shape and dye loading.

Further, the FI measurement achieved from using flow cytometry may also vary, even among population of uniform particles.

Figure 6:
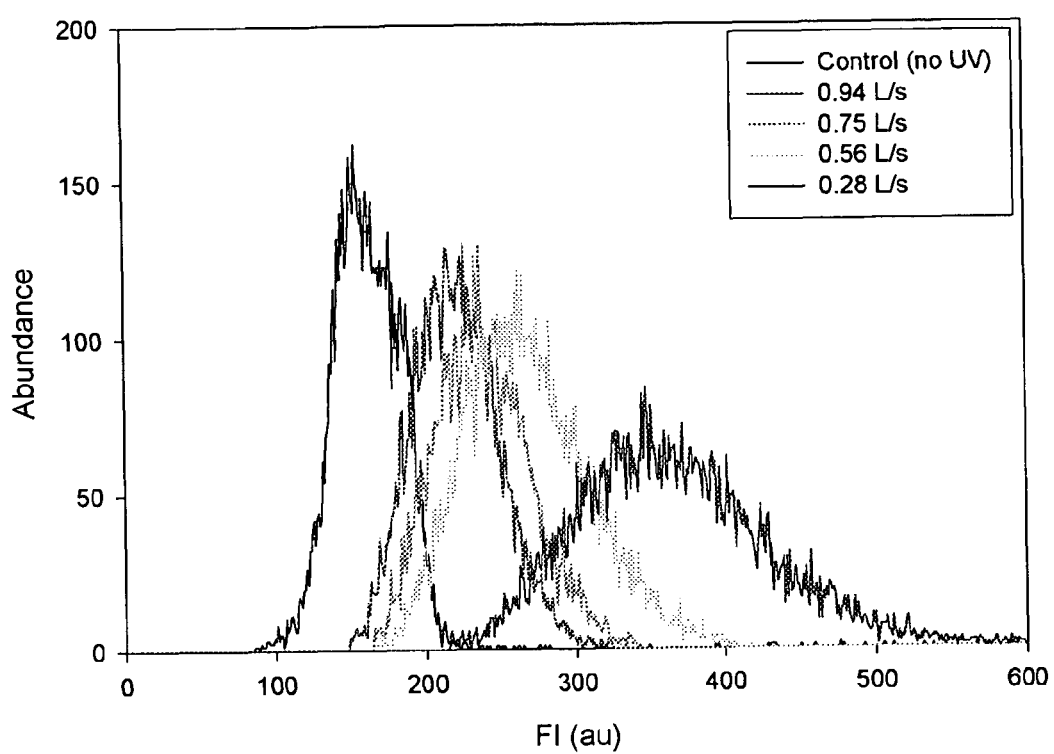
FIG. 6 is a graphical representation of fluorescence intensity distributions of dyed microspheres generated using a continuous flow reactor.
Figure 7A:
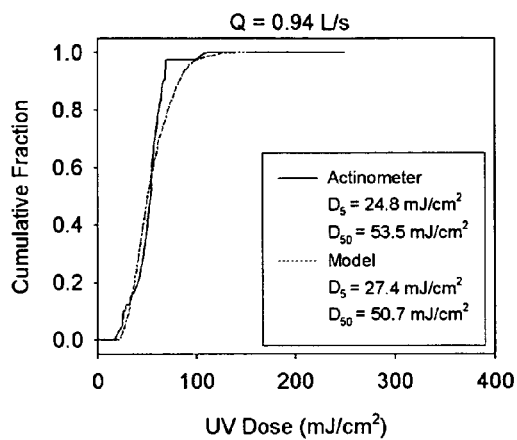
FIGS. 7A-D are illustrations of cumulative UV dose distributions delivered by a continuous flow UV reactor.
Figure 7B:
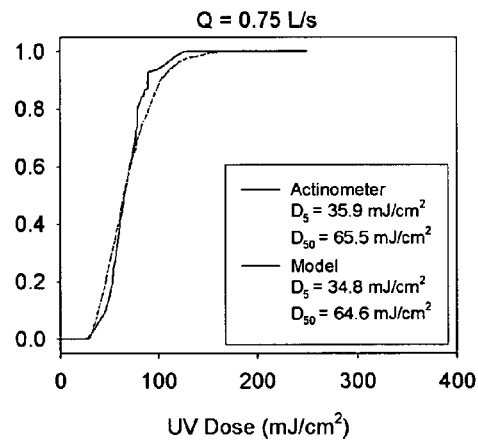
Figure 7C:
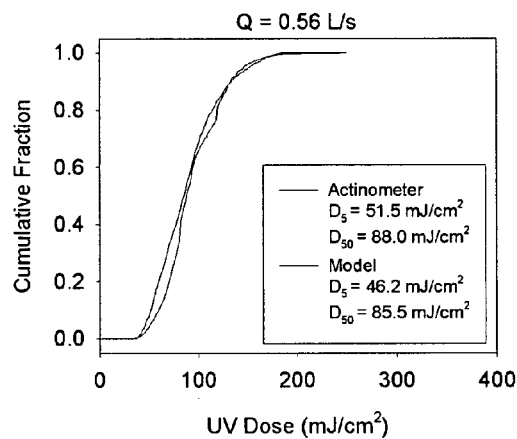
Figure 7D:
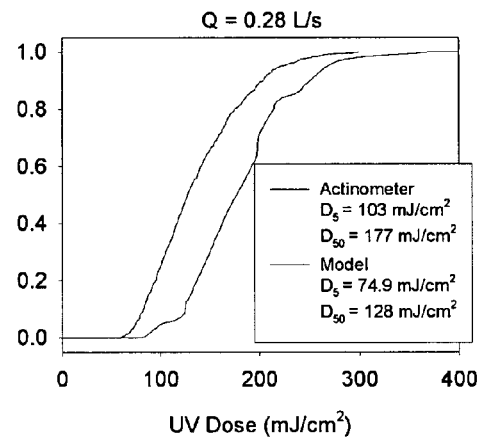

FIG. 6 illustrates the results of the flow cytometry analysis of extracted samples collected from a continuous-flow reactor. The results may be illustrated using the FI distribution in the system. FIG. 6 also illustrates the relationship of FI at varying flow rates. The range of the flow rates may be from about 28 L/s to about 0.94 L/s. As flow rate increases, the duration of UV exposure will decrease.

In practicing the method, mathematical algorithms may be used to calculate the dose distribution passing through the flow-through reactor. The algorithm allows differentiation and separation of the sources of FI variation that exist in the analysis of dyed microsphere collections from a continuous-flow reactor by flow cytometry.

In particular, measurements of FI for microspheres collected from a continuous-flow rector are attributable to the dose distribution, as well as variations in the characteristics of the microspheres and error that is inherent in the measurement of FI by flow cytometry or other methods of FI measurement for microsphere populations.

The latter two sources of error specifically, microsphere variation and variation associated with the analytical method used to measure FI, can also be present in the results of analysis of FI for samples that are UV irradiated under a collimated beam or an alternate device. Therefore, a deconvolution algorithm may be used to subtract these variations from the total variation seen in analysis of extracted samples from the continuous-flow reactor. The result is an estimate of the dose distribution.

In analyzing the FI responses of microspheres that are subjected to a well-defined single-valued UV dose from the collimated-beam procedure, the calculation may be formally defined in the following formula:

$$\sum_{j=0}^{n} \Gamma_{j,i} \equiv 1 \sum_{i,j} \Gamma_{j,i} \equiv m+1$$

In this equation, the definitions are formally provided as: i is an index for counting dose (D) increments (bin width=1 mJ/cm$^2$; i=1, 2, ..., m); j is an index for counting FI increments (bin width=1 FI unit; j=1, 2, ..., n); $C_{j,i}$ is the number of microspheres that emit $FI_j$ after being subjected to dose $D_i$; $C_i$ is the number of microspheres counted by flow cytometry in sample subjected to $D_i$ (this can also be represented by $$\sum_{j=0}^{n} C_{j,i});$$

$\Gamma_{j,i}$ is the fraction of particles receiving $D_i$ that emit $FI_j$ (this can also be represented by $$\frac{C_{j,i}}{C_i}\right).$$

An alternate mathematical approach may be used for estimating an unknown dose distribution calculated by deconvolution of the properties of the dyed microsphere exposures under the collimated beam and the microsphere exposures from the flow-through reactor. The mathematical formula may be used to calculate the microspheres that have been subjected to a single value dose. The formula may be formally defined as follows:

$$\sum_{i=0}^{m} \alpha_i \equiv 1 \quad \sum_{j=0}^{n} \beta_j \equiv 1$$

In this equation, the definitions may be provided as follows: A is the total number of FI measurements collected for a sample; $A_i$ is the number of particles in a sample that receive dose $D_i$; $\alpha_i$ is the fraction of particles in a mixed sample that receive dose $D_i$ (this can also be represented by $$\frac{A_i}{A});$$

$B_j$ is the number of particles in a sample that emit $FI_j$, $\beta_j$ is the fraction of particles in a sample that emit $FI_j$ (this can also be represented by $$\frac{B_j}{A}).$$

Alternatively, by using UV irradiating microspheres under a collimated beam, a collection of microspheres subjected to a single-valued dose may be identified. The dose-response calculation process described above, and illustrated in FIG. 5, involves using the dose-response calculation over a range of UV doses. Extracting a small fragment from each of the exposed batches of dyed microspheres illustrated in FIG. 5, may be combined together to yield a known dose distribution.

Using the known dose distribution, the FI distribution in the mixed sample ($B_j$ or $\beta_j$) may be represented as a linear combination of the FI distributions of each individual portion used initially to develop the mixed batch as well as the fraction that each individual dose comprises in the overall mixed batch.

The mathematical formula may be formally represented as follows:

$$B_j = \alpha_0 A \Gamma_{j,0} + \alpha_1 A \Gamma_{j,1} + \ldots + \alpha_m A \Gamma_{j,m} = \sum_{i=0}^{m} \alpha_i A \Gamma_{j,i}$$

or alternatively, the mathematical formula may be represented by dividing through by A:

$$\beta_j = \sum_{i=0}^{m} \alpha_i \Gamma_{j,i}$$

The dose-response data extracted using the collimated-beam procedure, as shown in FIG. 5, can provide detailed information of the FI distribution behavior of the dyed microspheres over the range of relevant doses for the UV reactor. When using numerical deconvolution, the FI distributions of the dyed microspheres (i.e., microsphere dose-response behavior) may be represented as a smaller dose interval that described the collimated-beam procedure. To achieve consistency of the bin width used to represent the dose distribution the value of 1 mJ/cm² may be used. Preferably, the dose increments should be at least about 0-200 mJ/cm2. Frequently, changes in FI distribution also vary in the range of doses between 0-200 mJ/cm2. Consequently, an interpolation procedure may be used to characterize the dose-response behavior as desired.

In another alternate method, a Weibull distribution having a location parameter, sometimes referred to as a three parameter Weibull distribution provides a close fir to the individual dose distributions as illustrated in FIG. 5. The location, scale and shape of the graphical representation may vary in the linear direction depending on the range of doses used in the system. Preferably, a regression fit model of these linear trends, numerical values used in matrix $\Gamma$ may be estimated using interpolation.

In yet another method, the mathematical representation of the convolution algoritm may be defines in the above reference formulas. The mathematical equations may be rewritten in matrix notation. The formula is formally defined as:

$\beta = \Gamma \times \alpha$, where $$\beta = \begin{Bmatrix} \beta_0 \\ \beta_1 \\ \vdots \\ \beta_n \end{Bmatrix}; \quad \Gamma = \begin{Bmatrix} \gamma_{0,0} & \gamma_{0,1} & \cdots & \gamma_{0,m} \\ \gamma_{1,0} & \gamma_{1,1} & \cdots & \gamma_{1,m} \\ \vdots & \vdots & \vdots & \vdots \\ \gamma_{n,0} & \gamma_{n,1} & \cdots & \gamma_{n,m} \end{Bmatrix}; \quad \alpha = \begin{Bmatrix} \alpha_1 \\ \alpha_1 \\ \vdots \\ \alpha_m \end{Bmatrix}$$

The objective of the deconvolution step is to yield an estimate of the dose distribution, which is represented by the vector $\alpha$ in the above reference equation. For each operating condition, the vector $\beta$ can represent the FI distribution calculated using the flow cytometry analysis of an effluent sample from the continuous-flow reactor, as previously shown in FIG. 4. The matrix $\Gamma$ is calculated using the interpolation algorithm (i.e. the Weibull distribution) and the data generated from the flow cytometry analysis of exposed microspheres under the collimated beam. The deconvolution process may be achieved by importing data from the flow cytometry analyses into a MATLAB program or equivalent program subject the definitions discussed in the first three equations.

FIGS. 7A-D illustrate the deconvolved dose distributions using a nominal transmittance condition of 99%. The dose distributions may be represented as cumulative distribution functions. Additionally, the estimates of the dose distribution based on application of a Lagrangian numerical simulation are also provided in FIGS. 7A-D for comparison. Dose distribution estimates by the two methods are in good agreement. Consequently, UV reactor analysis by application of dyed microspheres and the related methods described herein yields a more comprehensive description of UV reactor behavior and performance than existing methods, such as biodosimetry A method of using dyed microspheres for measurement of the ultraviolet dose distribution delivered by a continuous flow UV reactor is shown in FIG. 8. The method 100 includes: introducing microspheres labeled with a photochemically-active compound in a UV reactor 102; harvesting the dyed microspheres downstream of the irradiated zone of the UV reactor 104; exposing the labeled microspheres to UV irradiation under a collimated beam of UV irradiation and quantifying a UV dose behavior 106; conducting fluorescence intensity measurement on the labeled microspheres from the UV reactor 108; developing an estimate of a dose distribution by the reactor by numerical deconvolution of the sum of the UV dose response behavior and fluorescent intensity of exposed microspheres 110; and quantifying predication of the ability of the photochemical reactor dynamics 112.

With this method, quantitative predictions of the ability of a photochemical reactor to inactivate any microorganism may be achieved. The same method may be used to make quantitative predictions of the efficiency of a photochemical reactor for essentially any photochemical transformation (i.e., applications are not be limited to photochemical reactors used for disinfection). In addition, this method may be used to validate photochemical reactor performance, and to compare with valid predictions of numerical models, such as the Lagrangian model described above.

It is therefore intended that the foregoing detailed description be regarded as illustrative rather than limiting, and that it be understood that it is the following claims, including all equivalents, that are intended to define the spirit and scope of this invention.

We claim:

1. A method for measuring ultraviolet dose exposure in a photochemical reactor, comprising the steps of:
   a. introducing a plurality of unirradiated dye molecules attached to a microsphere into a photochemical reactor;
   b. exposing the unirradiated dye molecules to an ultraviolet radiation at a first wavelength effective to photochemically convert at least a portion of the unirradiated dye molecules to fluorescent dye molecules attached to the microsphere within the photochemical reactor;
   c. irradiating the fluorescent dye molecules at a second wavelength effective to cause fluorescence of the fluorescent dye molecules at a third wavelength; wherein the unirradiated dye molecules not photochemically converted to the fluorescent dye molecules when exposed to the first wavelength do not fluoresce at the third wavelength when irradiated with radiation at the second wavelength;
   d. detecting the fluorescence of at least a portion of the fluorescent dye molecules at the third wavelength; and
   e. correlating at least a portion of the fluorescence detected at the third wavelength to an ultraviolet radiation dose distribution from the photochemical reactor, the ultraviolet radiation dose distribution representing a plurality of fractions of the unirradiated dye molecules that received correspondingly different ultraviolet dose exposures to the ultraviolet radiation including at least the portion that were converted to the fluorescent dye molecules, the ultraviolet dose exposure is defined as the time-integral of ultraviolet intensity history over a period of exposure; wherein the unirradiated dye molecule is attached to the microsphere in a manner that does not substantially diminish the fluorescence of the fluorescent dye molecules at the third wavelength so as to allow for quantifiable detection of the fluorescence, wherein the microsphere is coated with streptavidin, the unirradiated dye molecule is attached to the microsphere by a chemical structure of the formula: M-S—B-L-D, wherein:
   M represents the surface of the microsphere,
   —S represents the streptavidin attached to the surface of the microsphere,
   —B represents a biotin molecule attached to the streptavidin;
   —L represent a hydrophilic linking group;
   —D represents the dye molecule according to a formula of:

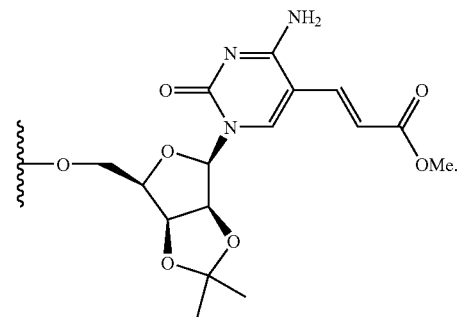

2. The method of claim 1, further comprising the step of: measuring the ultraviolet dose-response behavior of the photochemical conversion of the unirradiated dye molecules to fluorescent dye molecules.

3. The method of claim 2, wherein measurement of the ultraviolet dose-response behavior comprises the steps of:
   a. providing a first aqueous suspension comprising a plurality of unirradiated dye molecules attached to microspheres;
   b. exposing the first aqueous suspension to a collimated ultraviolet radiation at the first wavelength and a first test dose wherein the first wavelength and the first test dose is effective to photochemically convert at least a portion of the unirradiated dye molecules to fluorescent dye molecules within the aqueous suspension;
   c. irradiating the fluorescent dye molecules from the first aqueous suspension at the second wavelength in a manner effective to cause fluorescence of the fluorescent dye molecules at the third wavelength;
   d. detecting the fluorescence of at least a portion of the fluorescent dye molecules in the first aqueous suspension at the third wavelength;
   e. repeating steps a.-d. on one or more aqueous suspensions of unirradiated dye molecules attached to microspheres, while exposing each aqueous suspension to collimated ultraviolet radiation at the first wavelength at different test doses representative of the range of doses that can be delivered by the photochemical reactor.

4. The method of claim 3, wherein a plurality of aqueous samples comprising unirradiated dye molecules are exposed to a first wavelength that is a germicidal ultraviolet wavelength and a plurality of test doses of the collimated ultraviolet radiation between about 0 and 200 mJ/cm$^2$.

5. The method of claim 1, wherein detection of the fluorescence of the fluorescent dye molecule comprises the step of measuring the fluorescence intensity of the irradiated fluorescent dye molecule using flow cytometry.

6. The method of claim 1, wherein the unirradiated dye molecule is a non-fluorescent molecule.

7. The method of claim 1, wherein the fluorescent dye molecule includes a pyrido[2,3-d]pyrimidine moiety.

8. The method of claim 1, wherein the microsphere is coated with streptavidin, and the unirradiated dye molecule is attached to the microsphere by a chemical structure of the formula:

M-S—B-L-D, wherein:
M represents the surface of the microsphere,
—S represents the streptavidin attached to the surface of the microsphere,
—B represents a biotin molecule attached to the streptavidin,
—L represents a hydrophilic linking group comprising a moiety of the formula:

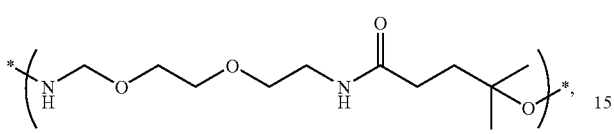

and
—D represents the dye molecule attached to the hydrophilic linking group.

9. The method of claim 1, wherein the microsphere is coated with streptavidin, the unirradiated dye molecule is attached to the microsphere by a chemical structure of the formula: M-S—B-L-D,
wherein:
M represents the surface of the microsphere, —S represents the streptavidin attached to the surface of the microsphere,
—B-L-D represents a compound of the formula:

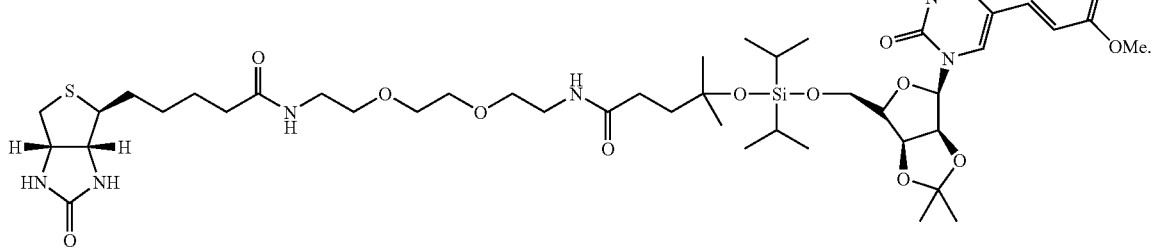

10. The method of claim 1, wherein the photochemical reactor is a continuous-flow photochemical reactor, and the method further comprising the steps of:
  a. measuring the fluorescence intensity of the irradiated fluorescent dye molecule using flow cytometry;
  b. measuring the ultraviolet dose-response behavior of the photochemical conversion of the unirradiated dye molecules to fluorescent dye molecules from collimated ultraviolet radiation; and
  c. estimating the UV dose distribution in the photochemical reactor by numerical deconvolution of the fluorescence intensity measurements of samples collected from the continuous flow photochemical reactor and measuring the ultraviolet dose-response behavior as defined by the fluorescence intensity measurements from the samples exposed to the collimated ultraviolet radiation.

11. The method of claim 1, further comprising the steps of:
  a. measuring the fluorescence intensity of the irradiated fluorescent dye molecule using flow cytometry;
  b. measuring the ultraviolet dose-response behavior of the photochemical conversion of the unirradiated dye molecules by performing the steps of:
    1. providing a first aqueous suspension comprising a plurality of unirradiated dye molecules attached to microspheres;
    2. exposing the first aqueous suspension to a collimated ultraviolet radiation at the first wavelength and a first test dose between about 0 and 200 $mJ/cm^2$; wherein the first wavelength is effective to photochemically convert at least a portion of the unirradiated dye molecules to fluorescent dye molecules within the aqueous suspension;
    3. irradiating the fluorescent dye molecules from the first aqueous suspension at the second wavelength in a manner effective to cause fluorescence of the fluorescent dye molecules at the third wavelength;
    4. detecting the fluorescence of at least a portion of the fluorescent dye molecules in the first aqueous suspension at the third wavelength;
    5. providing a second aqueous suspension comprising a plurality of unirradiated dye molecules;
    6. exposing the second aqueous suspension to collimated ultraviolet radiation at the first wavelength and a second test dose between about 0 and 200 mJ/cm.sup.2, wherein the second test dose is different from the first test dose;
    7. irradiating the fluorescent dye molecules from the second aqueous suspension at the second wavelength;
    8. detecting the fluorescence of at least a portion of the fluorescent dye molecules in the second aqueous suspension at the third wavelength;
    9. comparing the fluorescence detected from the first aqueous suspension and the fluorescence detected from the second aqueous suspension;
    10. calculating the ultraviolet dose-response of the photochemical conversion of the unirradiated dye molecule to fluorescent dye molecules from the comparative fluorescence of the first aqueous solution and the second aqueous solution; and
  c. estimating the UV dose distribution in the photochemical reactor by numerical deconvolution of the fluorescence intensity measurements and the measured ultraviolet dose-response behavior; and
  wherein the microsphere is coated with streptavidin, and the unirradiated dye molecule is attached to the microsphere by a chemical structure of the formula:

M-S—B-L-D, wherein:

M represents the surface of the microsphere,

—S represents the streptavidin attached to the surface of the microsphere,

—B represents a biotin molecule attached to the streptavidin,

—L represents a hydrophilic linking group comprising a moiety of the formula:

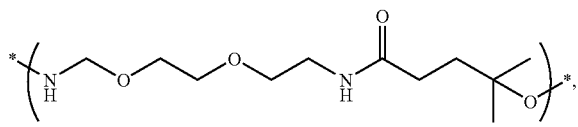

and

—D represents the dye molecule attached to the hydrophilic linking group.

12. The method of claim 11, wherein: —B-L-D represents a compound of the formula:

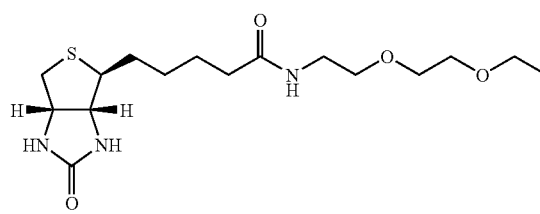

13. A method for measuring ultraviolet dose in a photochemical reactor, comprising the steps of:
   a. providing a continuous flow photochemical reactor comprising a fluid stream passing from an upstream portion through an irradiated zone wherein the fluid stream is exposed to ultraviolet radiation at a first wavelength in the irradiated zone;
   b. introducing a first plurality of microparticles comprising unirradiated dye molecules into the upstream portion of the fluid stream within the continuous flow ultraviolet reactor;
   c. exposing the first plurality of microparticles to the ultraviolet radiation within the irradiated zone, wherein the first wavelength is effective to photochemically convert at least a portion of the unirradiated dye molecules to fluorescent dye molecules within the photochemical reactor;
   d. subsequently irradiating the first plurality of microparticles at a second wavelength effective to cause fluorescence of the fluorescent dye molecules at a third wavelength; wherein the unirradiated dye molecules not photochemically converted to the fluorescent dye molecules when exposed to the first wavelength do not fluoresce at the third wavelength when irradiated with radiation at the second wavelength; and
   e. detecting the fluorescence intensity of the first plurality of fluorescent dye molecules at the third wavelength;
   f. measuring the ultraviolet dose-response behavior of the photochemical conversion of a second plurality of unirradiated dye molecules attached to microspheres;
   g. estimating the UV dose distribution in the photochemical reactor by numerical deconvolution of the fluorescence intensity measurements detected and the measured ultraviolet dose-response behavior, the UV dose distribution representing a plurality of fractions of the unirradiated dye molecules that received correspondingly different ultraviolet dose exposures to the ultraviolet radiation including at least the portion that were converted to the fluorescent dye molecules, the ultraviolet dose exposure is defined as the time-integral of ultraviolet intensity history over a period of exposure;
   wherein the unirradiated dye molecule is attached to a microsphere, and the unirradiated dye molecule is (E)-5-[2-(methoxycarbonyl)ethenyl]cytidine.

14. The method of claim 13, wherein the first plurality of unirradiated dye molecule is measured using flow cytometry.

15. The method of claim 13, wherein the first wavelength is a germicidal ultraviolet wavelength.

16. The method of claim 13, wherein measurement of the ultraviolet dose-response behavior wherein measurement of the ultraviolet dose-response behavior comprises the steps of:
   a. providing a first aqueous suspension comprising a plurality of unirradiated dye molecules attached to microspheres;
   b. exposing the first aqueous suspension to a collimated ultraviolet radiation at the first wavelength and a first test dose between wherein the first wavelength is effective to photochemically convert at least a portion of the unirradiated dye molecules to fluorescent dye molecules within the aqueous suspension;
   c. irradiating the fluorescent dye molecules from the first aqueous suspension at the second wavelength in a manner effective to cause fluorescence of the fluorescent dye molecules at the third wavelength;
   d. detecting the fluorescence of at least a portion of the fluorescent dye molecules in the first aqueous suspension at the third wavelength;
   e. repeating steps a.-d. on one or more aqueous suspensions of unirradiated dye molecules attached to microspheres, while exposing each aqueous suspension to collimated ultraviolet radiation at the first wavelength at different test dose levels representative of the range of doses that can be delivered by the photochemical reactor.

* * * * *